United States Patent
Ansley

(10) Patent No.: US 6,398,092 B1
(45) Date of Patent: Jun. 4, 2002

(54) CARPENTER'S BELT WITH LUMBOSACRAL SUPPORT, LOOPED INTERCHANGEABLE POUCHES, AND SNAPS FOR SUSPENDERS

(76) Inventor: Michael R. Ansley, 35W 322 Fox Dr., Saint Charles, IL (US) 60174

( * ) Notice: Subject to any disclaimer, the term of this patent is extended or adjusted under 35 U.S.C. 154(b) by 0 days.

(21) Appl. No.: 09/617,562

(22) Filed: Jul. 17, 2000

(51) Int. Cl.[7] .............................................. A45C 15/00
(52) U.S. Cl. ........................ 224/582; 224/662; 224/665; 224/677; 224/680; 224/682; 224/901.8; 224/904
(58) Field of Search ................................ 224/582, 583, 224/662, 665, 677, 682, 680, 901.8, 904

(56) References Cited

U.S. PATENT DOCUMENTS

| | | | | | |
|---|---|---|---|---|---|
| 3,171,409 A | * | 3/1965 | Cetrone | ........................ | 128/99 |
| 4,384,372 A | * | 5/1983 | Rector | ........................... | 2/300 |
| 4,747,527 A | * | 5/1988 | Trumpower, II | ............ | 224/224 |
| 4,923,105 A | * | 5/1990 | Snyder | ........................ | 224/255 |
| 4,962,873 A | * | 10/1990 | Schattel | ...................... | 224/226 |
| 5,349,706 A | * | 9/1994 | Keer | .............................. | 2/300 |
| 5,388,274 A | * | 2/1995 | Glover et al. | .................. | 2/338 |
| 5,413,262 A | * | 5/1995 | Dewire et al. | ............... | 224/253 |
| 5,464,136 A | * | 11/1995 | Eddy | .......................... | 224/252 |
| 5,484,395 A | * | 1/1996 | DeRoche | .................... | 2/311 X |
| 5,497,923 A | * | 3/1996 | Pearson et al. | ............. | 224/253 |
| 5,505,356 A | * | 4/1996 | Noriega et al. | ............. | 224/250 |
| 5,683,022 A | * | 11/1997 | Evans | ......................... | 224/583 |
| 5,894,976 A | * | 4/1999 | Harper | ........................ | 224/587 |
| 6,213,365 B1 | * | 4/2001 | Stocke et al. | ............... | 224/665 |

* cited by examiner

Primary Examiner—Stephen K. Cronin
(74) Attorney, Agent, or Firm—John L. Schmitt

(57) ABSTRACT

An improved rigid carpenter's belt with lumbosacral support includes end sections to accept a plurality of interchangeable looped carpenter pouches with Velcro strips to attach the pouches to corresponding Velcro strips on the carpenter belt. The belt comprises a belt structure of leather having a buckle on one end and holes in the other end to form a releasable coupling and a central section of increased height, cephalad and caudoly, to provide lumbosacral support extending laterally within the central section and fabricated of foam-like material covered with split leather. Laterally disposed on opposite sides of the lumbosacral support.

6 Claims, 3 Drawing Sheets

CARPENTER'S BELT WITH LUMBOSACRAL SUPPORT, LOOPED INTERCHANGEABLE POUCHES, AND SNAPS FOR SUSPENDERS

BACKGROUND OF THE INVENTION

1. Field of the Invention

The present invention relates to belts supporting the back for carpentry and more particularly to carpentry belts that incorporate a form fitting lumbosacral support. More particularly the present invention is a rigid belt design that gives a form fitted lumbosacral support and is tapered to accept leather looped carpenter's pouches which the ends of the belt slip through also the tapered ends increases the carpenter's range of motion.

2. Description of the Prior Art

Low back pain is still one of the major health hazards in the U.S. Improper lifting; heavy lifting, repetitive work stress all can lead to back injury. Rigid belts provides good support with a form fitted lumbosacral pad but has shown that it restricts range of motion. The present invention is directed at improving on the rigid belt by tapering the belt down on both sides to free up a workers range of motion. This will also make the leather belt able to accept loop carpenter's pouches. The rigid support belt will hold the full pouches more securely then a flexible belt and direct the load of the pouches more evenly throughout the belt. The carpenter's belt has snaps built in for suspenders to aid in weight distribution. With this improved design carpenters will be able to have the rigid former fitted lumbosacral support while lifting and also now have freedom of motion not otherwise had in rigid support belt.

For example U.S. Pat. No. 5,484,395 to Silverstolpe 35 et. al. discloses a fireman's back brace including a lumbar spinal support composed of flame retardant materials. But does not taper to accept carpenter's looped pouches nor is it a rigid support, nor does it support the sacrum.

In U.S. Pat. No. 5,349,706 to Keer et al. a belt with lumbar support has pouch support strap located on the belt laterally, pouch support straps located on the belt laterally disposed on opposite sides of the lumbar support for receiving any one of a plurality of interchangeable pockets. This belt is tapered but not enough back to accept carpenter's looped pouches and also decreases range of motion. Also it has elastic panels which turns away from a true rigid belt design will decrease in distributing the load of the pouches through out the belt. Also it does not support the sacrum by extending caudoly.

In U.S. Pat. No. 4,747,527 to Trumpower et al. a belt uses a snaplock assembly for the tool or equipment receiver. This belt is not tapered to receive looped pouches would restrict range of motion also is not high and low enough in back for good lumbar/sacral support.

In U.S. Pat. No. 3,171,409 to Cetrone et al. the belt width is only 1 9/16" not wide enough for good lumbosacral padded support.

In U.S. Pat. No. 5,388,274 to Glover et al. is a flexible belt that does have a lumbar and sacral pad. But does not taper to accept looped leather carpenter's pouches, or have snaps attached for suspenders to aid in weight distribution. Therefore it can be appreciated that there exists a continuing need for new and improved carpenter's belt with lumbosacral support that can accept carpenter's looped pouches that can limit back stress during lifting of heavy objects, and that has snaps for suspenders to aid in weight distribution. The course of a carpenter's operations in this regard, the present invention substantially fulfills this need. The present invention achieves its intended purposes, objects and advantages through a new useful and unobvious combination of method steps and component elements. At reasonable cost to manufacture, and by employing only readily available materials.

SUMMARY OF THE INVENTION

In view of the foregoing disadvantages inherent in the known types of lumbosacral support belts, the present invention is an improved carpenter's belt. This belt provides lumbosacral support for a carpenter while the carpenter is performing carpenter duties. As such, the general purpose of the present invention, which will be described subsequently in greater detail, is to provide a new and improved carpenter's belt with lumbosacral support, and with end sections to accept looped carpenter pouches which the ends of the belt slip through, and with snaps built in for suspenders to aid in weight distribution giving increased range of motion to a rigid belt.

Therefore, it is an object of the present invention to provide an improved carpenter's belt with lumbosacral support and end sections to accept looped carpenter pouches and built-in snaps to attach suspenders for improved weight distribution.

It is therefore an additional object of the present invention to provide a new and improved carpenter's belt with lumbosacral support and end sections to accept looped carpenter pouches which has all of the advantages of the prior art.

It is another object of the present invention to provide a new and improved carpenter's belt with lumbosacral support which may be easily and efficiently manufactured and marketed.

It is a further object of the present invention to provide a new and improved carpenter's belt with lumbosacral support that is durable and reliable.

Still, another object of the present invention is to provide a new and improved carpenter's belt with lumbosacral support having end sections to accept looped carpenter pouches and corresponding Velcro strips on the pouches and belt to stop the pouches from moving.

Yet another object of the present invention is to provide a new and improved carpenter's belt with lumbosacral support to improve the range of motion of the carpenter while still supplying rigid lumbosacral support.

These together with other objects of the invention, along with the various features of the novelty which characterize the invention, are pointed out with particularly in the claims annexed to and forming a part of this disclosure. For a better understanding of the invention, its operating advantages and specific objects attained by its uses, reference should be had to the accompanying drawings and descriptive matter in which there is illustrated preferred embodiment of the invention. The foregoing has outlined some of the more pertinent objects of this invention. These objects should be construed to merely illustrative of some of the more prominent features and applications of the present invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF DESCRIPTION OF THE DRAWINGS

The invention will be better understood and objects other than those set forth above will become apparent when consideration is given to the following detailed description of the annexed drawings.

DESCRIPTION OF THE PREFERRED EMBODIMENT

Figure 6:
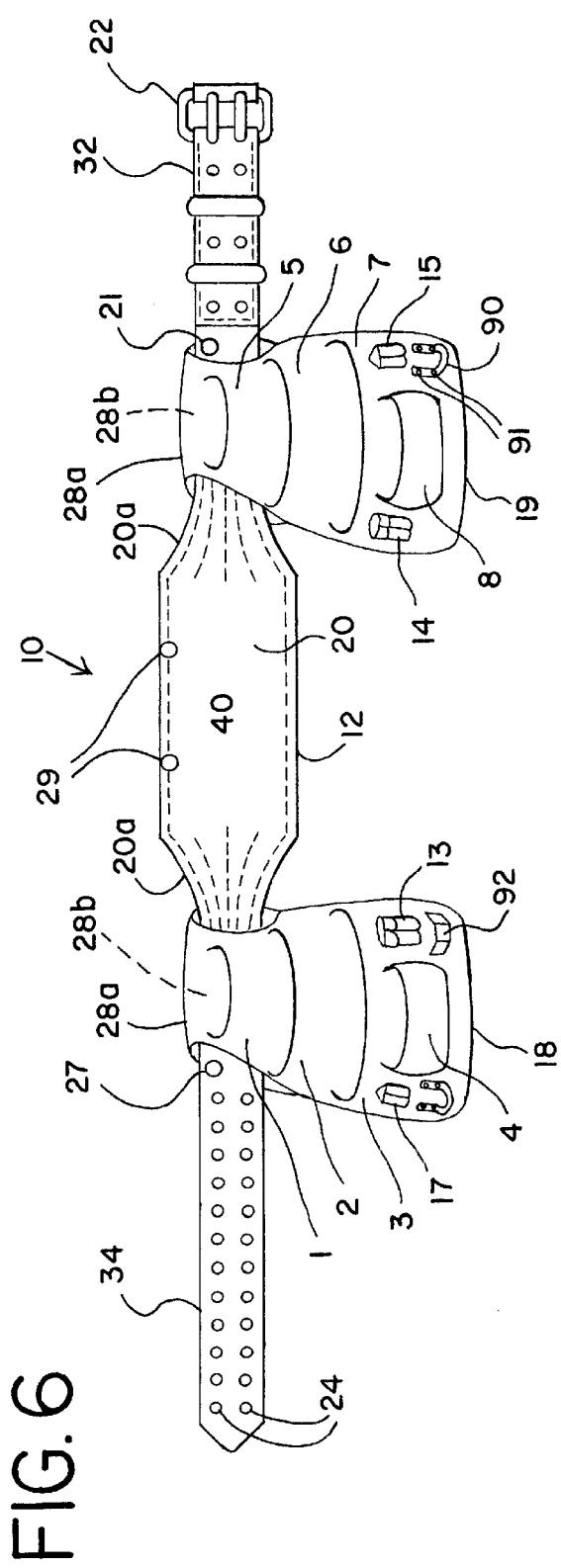
FIG. 6 is an elevation view of the carpenter's belt of FIG. 1 showing the belt with looped carpenter pouches carried by the belt.
Figure 7:
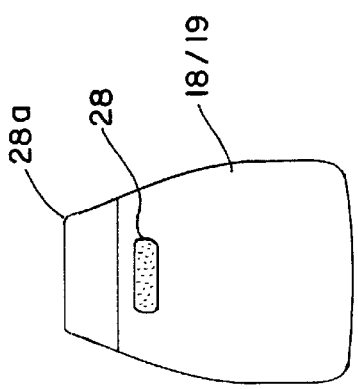
FIG. 7 is an elevation view of an inner side of the looped carpenter pouch with a loop of the pouch open to show a Velcro strip that attaches to a Velcro strip on the belt.

With reference to the drawings, and in particular to FIG. 6, a new and improved carpenter's belt with lumbosacral support is shown generally and designated 10. The belt 10 has end sections 32, 34 that slip through looped carpenter pouches 18, 19 and built-in snaps 21, 27 and 29 to attach suspenders.

From an overview standpoint, the carpenter's belt 10 with lumbosacral support includes a belt structure 12 having end sections 32, 34 that slip through loops 28a on respective upper ends of carpenter pouches 18, 19. The belt 10 is adapted for use by a carpenter and garment-like equipment the carpenter may wear.

More specifically, the belt structure 12 is constructed to have a buckle 22 on one end and holes 24 in the other end. The buckle 22 and holes 24 form a connectable coupling. During operation and use, the buckle 22 and holes 24 are located at the front of a wearer. A central section 20 of the belt structure 12 has an increased height, both cephalad and caudoly, for lumbosacral support. As worn during use, the central section 20 with its increased height both cephalad and caudoly, locates against a lumbosacral area of a back of the wearer, and the end sections 32 and 34 which are of a reduced height, locate at a front of the wearer. Tapering sections 20a couple the central section 20 of the belt structure 12 to the end sections 32, 34. Both end sections 32, 34 and the central section 20 of the belt structure 12 have permanently secured snaps 21, 27 and 29 to attach suspenders of the wearer. Additionally, both end sections 32, 34 have Velcro strips 25 and 26 to attach to their counterpart Velcro strips 28 on an inside of the loop 28a of each pouch 18, 19 to secure the position of these pouches 18, 19 on the belt 10.

Figure 1:
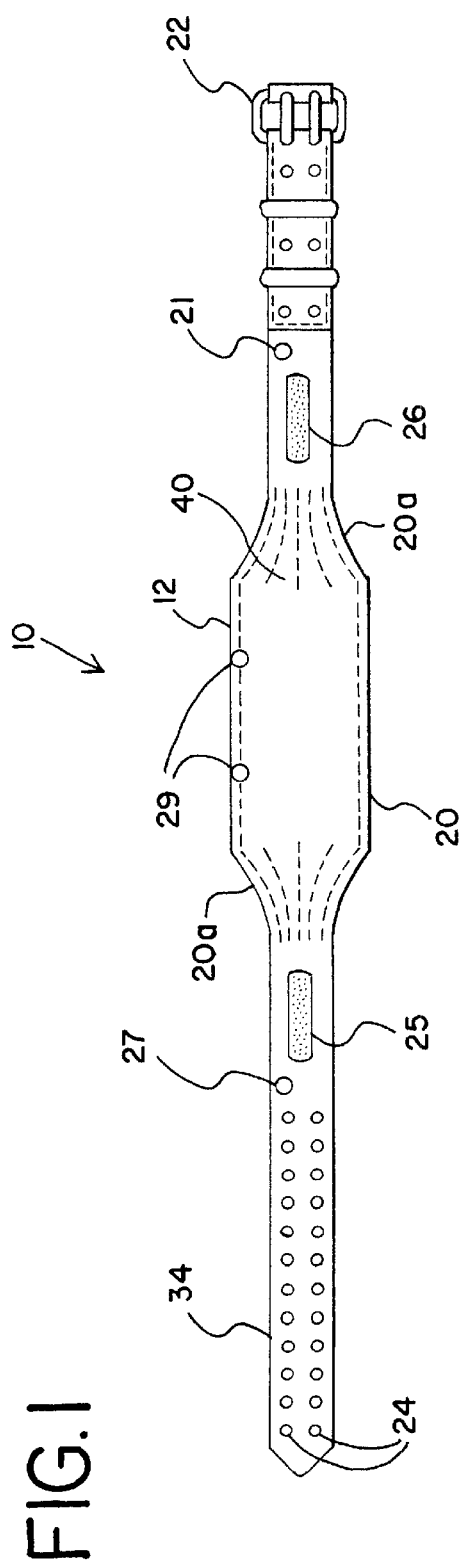
FIG. 1 is an elevation view of a carpenter's belt of this invention showing an outer side of the belt.
Figure 2:
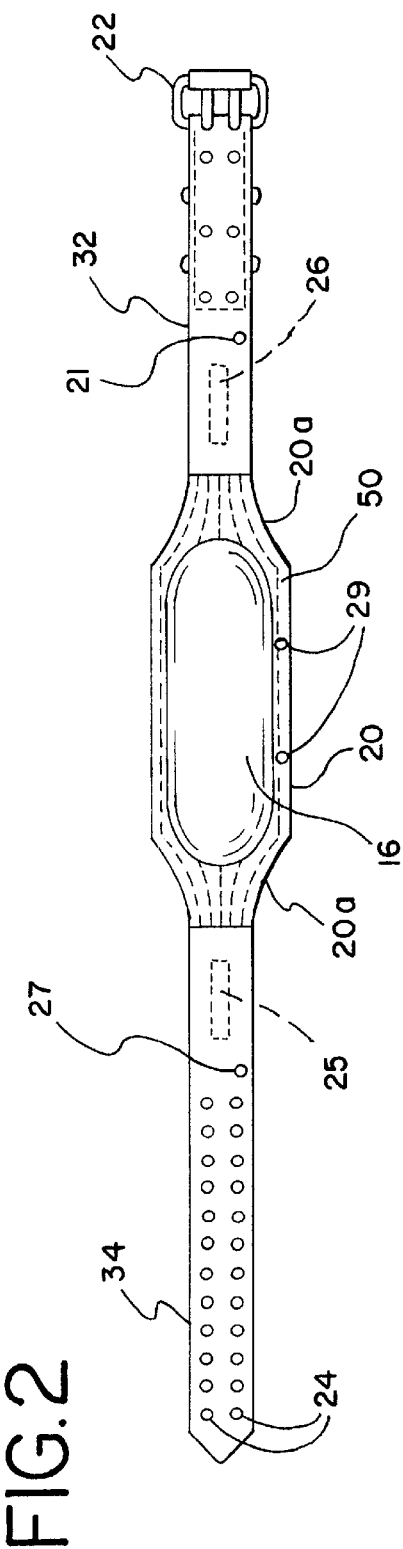
FIG. 2 is an elevation view of the carpenter's belt showing an inner side of the belt.
Figure 3:
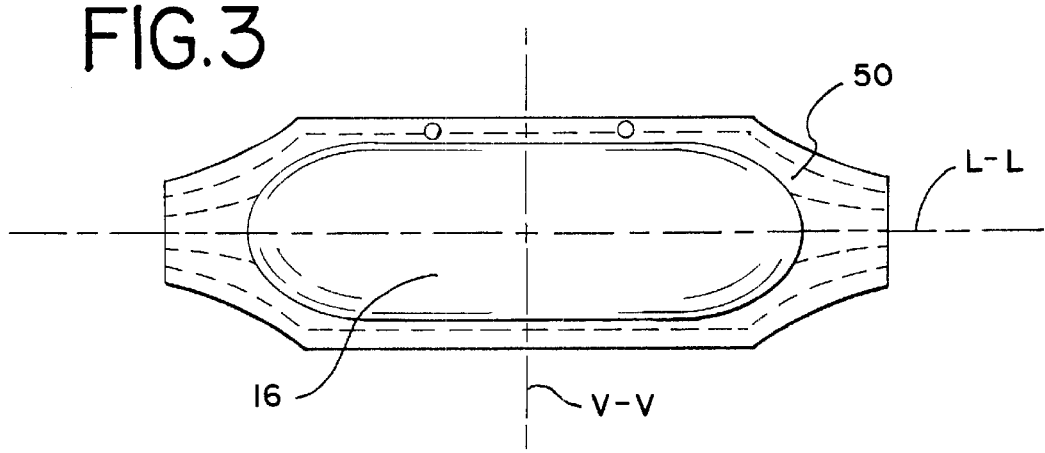
FIG. 3 is a detailed elevation view showing the inner side of a central section forming a lumbosacral support of the belt of FIG. 1.
Figure 4:
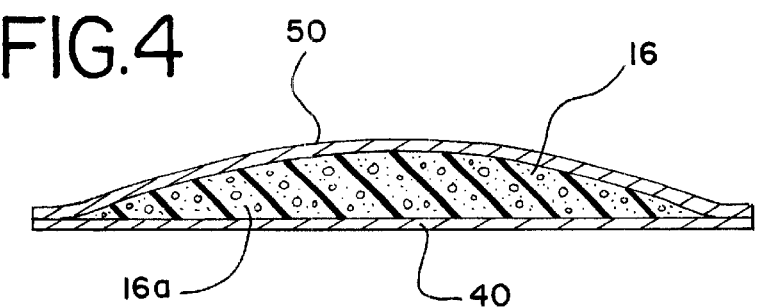
FIG. 4 is a cross sectional view as seen generally along the line 4—4 of FIG. 3.
Figure 5:
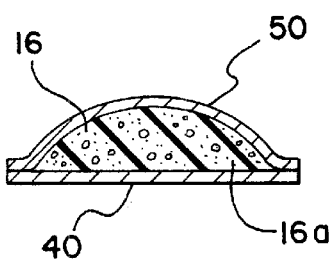
FIG. 5 is a cross sectional view as seen generally along the line 5—5 of FIG. 3.

The next major component of the belt 10 is a lumbosacral support 16. The lumbosacral support 16 includes a laterally and cephalad and caudadly extending foam-like component 16a see FIGS. 3–5. As formed, the support 16 has an inwardly vertical and horizontal convex-like shape with respect to the vertical axis V—V and longitudinal axis L—L. The height-to-length ratio of the support 16 is about one-to-four. This support 16 extends from a center portion of the wearer's back forward to the sides of the wearer. The support component 16a is located within the belt structure 12 between an exterior layer 40 and an interior layer 50 both formed of leather. An adhesive is used to hold the lumbosacral support component 16a in proper position between the layers 40 and 50 of the belt structure 12. Additionally, the periphery of the interior and exterior layers 50, 40 is stitched to secure the lumbosacral support component 16a in proper position between the layers 40 and 50 of the belt structure 12.

The interchangeable looped pouches 18 and 19 are shown in FIG. 6. The loops 28a each pouch 18, 19 includes an opening 28b that the end sections 32, 34 of the carpenter's belt 10 slip through. To secure the pouches 18, 19 to the belt structure 12, both end sections 32, 34 have a respective Velcro strip 25 and 26 to attach to their counterpart Velcro strips 28 which are inside the loops 28a of the pouches 18 and 19 to secure their position on the belt 10. Differently configured containers are provided on various pouches 18, 19. In FIG. 6, each pouch embodiment includes open pockets 1, 2, 3, 4, 5, 6, 7, and 8 and smaller pockets 13, 14, 15, and 17. Additionally, each pouch embodiment may include a rigid hook 90 attached by copper rivets 91 and a ruler clip 92. All pouches 18, 19 are leather and are riveted and stitched together.

The present invention is a carpenter's belt 10 which fits around a wearer's waist. The belt 10 is intended for carpenters who work with tools and prefer to have them on their person, within easy reach, without interfering with the freedom of motion of their arms, legs, and body. The carpenter's belt 10 having the lumbosacral support 16, end sections 32, 34, looped pouches 18, 19 and build-in snaps 21, 27 and 29 for suspenders provides a range of motion to the carpenter, distributes the weight of the belt 10 more evenly and gives rigid support to the lumbosacral area of the carpenter's back. The benefits of this belt 10 are very apparent. Carpenters and a majority of other trades could benefit greatly from this superior belt 10.

Therefore, the foregoing is considered as illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to, falling within the scope of the claims.

What is claimed as being new and desired to be protected by letters patent of the United States is as follows.

What is claimed is:

1. A new and improved carpenter's belt comprising:

a belt structure made of a semi-rigid material and having a buckle on one end and holes in an opposite end forming a connectable coupling at a front of a wearer of said belt and a central section forming a lumbosacral support at a back of said wearer, said support being inwardly convex-like and having an increased height, both cephalad and caudoly, that extends laterally about said wearer, said lumbosacral support formed in part of a foam-like material, a plurality of interchangeable looped pouches carried by said belt structure, said pouches having respective Velcro strips to attached said pouches to said belt structure by mating said pouch strips with corresponding Velcro strips on said belt structure, and a pair of snaps secured to said central section of said belt structure and snaps secured to respective upper edges of said belt structure near said buckle and said holes for attachment of suspenders of said wearer, wherein said lumbosacral support of said belt fits in a lumbosacral area of a back of said wearer of said belt to provide support to said wearer's back and thereby inhibit injury to said wearer's back as said wearer performs manual tasks.

2. A carpenter's belt as defined by claim 1 and further characterized by, said lumbosacral support having a height dimension less than a length dimension.

3. A carpenter's belt as defined by claim 2 and further characterized by, said lumbosacral support height dimension being less than one-half said length dimension.

4. A belt particularly adapted to provide support to a lumbosacral area of a back of a wearer of said belt and to carry tool pouches attached to said belt, said belt comprising:

a belt structure defined by spaced apart narrow end sections connected by an enlarged central section, a lumbosacral support carried by said central section, said support having a semi-stiff inner and outer side spaced apart by a soft inner component so that said support has an inwardly vertical and longitudinal convex-like shape prepared to form a complementary fit with said lumbosacral area of said wearer's back, and a releasable connection having a first part attached to an end of one said belt end section and second part attached to an end of said other belt end section, wherein with said belt positioned about a waist of said wearer and held thereabout by said releasable connection, said pouches filled with tools, and with said belt lumbosacral support fitted snugly against said lumbosacral area of said wearer's back, said belt inhibits injury to said wear as said wearer works with said tools.

5. A belt as defined by claim 4 and further characterized by, a vertical height of said convex shape of said lumbosacral support being less than a longitudinal length of said lumbosacral support.

6. A belt as defined by claim 4 and further characterized by, said central section connected to that end sections by respective tapering sections.

* * * * *